United States Patent
Israel et al.

(10) Patent No.: US 10,487,532 B2
(45) Date of Patent: Nov. 26, 2019

(54) STRUCTURES FORMED WITH SHEET MATERIAL CONFIGURED WITH AT LEAST ONE SOUND ABSORBING LAYER

(71) Applicants: Tara A. Israel, East Hampton, NY (US); Bonnie S. Schnitta, East Hampton, NY (US)

(72) Inventors: Tara A. Israel, East Hampton, NY (US); Bonnie S. Schnitta, East Hampton, NY (US)

(*) Notice: Subject to any disclaimer, the term of this patent is extended or adjusted under 35 U.S.C. 154(b) by 0 days.

(21) Appl. No.: 15/638,791

(22) Filed: Jun. 30, 2017

(65) Prior Publication Data

US 2017/0358289 A1    Dec. 14, 2017

Related U.S. Application Data

(63) Continuation-in-part of application No. 14/996,218, filed on Jan. 14, 2016, now Pat. No. 9,714,508.

(Continued)

(51) Int. Cl.

| | |
|---|---|
| *E04H 15/54* | (2006.01) |
| *G10K 11/168* | (2006.01) |
| *E04H 15/24* | (2006.01) |
| *A45F 3/22* | (2006.01) |
| *A01K 1/00* | (2006.01) |
| *E04B 1/86* | (2006.01) |

(52) U.S. Cl.
CPC .............. *E04H 15/54* (2013.01); *A01K 1/00* (2013.01); *A45F 3/22* (2013.01); *E04B 1/86* (2013.01); *E04H 15/24* (2013.01); *G10K 11/168* (2013.01)

(58) Field of Classification Search
CPC .......... E04H 15/54; E04H 15/18; E04H 15/36; E04H 2015/207; G10K 11/168; G10K 11/16; E04B 1/84; E04B 1/8209; E04B 1/8218
USPC .......... 135/96, 115, 124, 132–133, 136–137; 5/93.1, 113, 121, 414–415; 52/144–145; 181/198–200, 290, 284, 286
See application file for complete search history.

(56) References Cited

U.S. PATENT DOCUMENTS

| | | | | |
|---|---|---|---|---|
| 3,971,381 A | * | 7/1976 | Gibson | ............... A61L 15/225 |
| | | | | 604/366 |
| 4,403,677 A | * | 9/1983 | Messinger | ............... A47C 3/00 |
| | | | | 181/290 |

(Continued)

OTHER PUBLICATIONS

CN207728097U, pub.Aug. 14, 2018, "Flame retard tent sound absorb layer forming cloth acoustic panel adhere and fixed with substrate bottom waterproif" by Liu. (Year: 2018).*

*Primary Examiner* — Winnie Yip
(74) *Attorney, Agent, or Firm* — John F. Vodopia

(57) ABSTRACT

A structure formed with a frame structure and a sheet of material configured to reduce sound is wrapped around or otherwise surrounds the frame structure to form a hammock, basket, meditation pod, animal bed, snore reduction unit, wearable enclosure or other small structure, with an inner, sound limited or reduced volume. The sheet of material includes a base layer and at least one layer of sound-absorbing material, at least one layer of sound barrier material, or both, provided on or integral with the base layer. The sound limited or reduced volume includes an opening that may be closed or partially closed with a flap, canopy or hood. The flap, canopy or hood is preferably made of the same material at the sheet of material surrounding the frame.

12 Claims, 7 Drawing Sheets

Related U.S. Application Data

(60) Provisional application No. 62/103,633, filed on Jan. 15, 2015.

(56) References Cited

U.S. PATENT DOCUMENTS

| | | | | |
|---|---|---|---|---|
| 5,439,016 | A * | 8/1995 | Grahn | E04H 15/24 135/100 |
| 6,892,897 | B2 * | 5/2005 | Stewart | B65D 33/02 220/213 |
| 8,069,947 | B2 * | 12/2011 | Quasney | E04B 9/0428 181/224 |
| 8,136,626 | B1 * | 3/2012 | Aliev | F24F 13/24 181/198 |
| 8,646,571 | B2 * | 2/2014 | Aliev | H04M 1/19 181/198 |
| 8,807,275 | B2 * | 8/2014 | Wilson | E01F 8/0088 181/290 |
| 9,932,081 | B2 * | 4/2018 | Jensen | B62J 9/00 |
| 2003/0116379 | A1 * | 6/2003 | Khambete | B32B 11/04 181/290 |
| 2004/0212221 | A1 * | 10/2004 | Sato | B29C 44/1209 296/190.08 |
| 2005/0126848 | A1 * | 6/2005 | Siavoshai | B60R 13/0815 181/207 |
| 2014/0224578 | A1 * | 8/2014 | Blankenship | A47D 15/00 181/290 |

* cited by examiner

STRUCTURES FORMED WITH SHEET MATERIAL CONFIGURED WITH AT LEAST ONE SOUND ABSORBING LAYER

CROSS-REFERENCE TO RELATED APPLICATIONS

This application is a continuation-in-part (CIP) application of U.S. patent application Ser. No. 14/996,218, filed on Jan. 14, 2016 ("the parent application"), which parent application claims priority from U.S. Provisional Patent Application No. 62/103,633, filed Jan. 14, 2015; the contents of the patent application and the provisional application are incorporated herein by reference.

BACKGROUND OF THE INVENTION

The present invention is directed to a structure formed with sheet material, for example, a fabric formed with at least one sound absorbing layer, and/or at least one sound barrier layer, to limit an amount of unwanted sound (e.g., noise) entering a space or volume internal to the structure and/or an amount of sound generated within the internal space or volume and transmitted through the sound absorbing layer and/or the sound barrier layer to or from outside the structure.

There are a number of temporary or mobile structures designed for a range of needs, be it a tent for camping or a play fort for children. A tent or teepee, for example, may be constructed with purpose specific materials, so a camper can select a climate appropriate tent or a play fort can be made that is soft to the touch of a child.

For example, U.S. Pat. No. 8,978,816 discloses a sound-limiting acoustic shell by way of a hanging acoustic canopy. The intent of U.S. Pat. No. 8,978,816 is to create a portable acoustic shell that optimizes a musician's ability to hear what other players are performing under that same canopy. It also has in its design the ability to project sound so that it is better heard by an audience. Additionally, the absorbing material of this invention is designed to bring the decay time to a level that reduces the noise in the structure. Whereas this will make the speech or music sound better within the invention, a better sound is not the main goal of the NRC and STC of the invention, it is just a possible consequence.

SUMMARY OF THE INVENTION

The present invention overcomes the shortcomings of known arts, such as those mentioned above, for achieving a quantifiable level of desired or required quietude inside or outside a structure that can be portable if necessary.

To that end, the present invention provides a structure constructed with a sheet material formed that at least partially includes a sound absorbing layer and/or a sound barrier layer, to limit the amount of sound able to pass through the portion with the sound absorbing layer and/or sound barrier layer, into and out of the structure formed therewith. The sheet material may be any type of material that is flexible, such as cloth, including weaves, non-woven material and knits, bendable aluminum or metal, and organic or inorganic polymer sheets, such as vinyl, plastic sheeting, tarps or any material that can be formed into the desired structure shape. Preferably, the sheet material embodies a base fabric layer and the sound absorbing layer and/or the barrier layer is/are attached to or integral with one surface of the base layer in its entirety.

The sound absorbing material may be configured to absorb sound energy when sound waves collide with it, or pass by it, and inhibits sound waves that attempt to pass through the material, as opposed to reflecting the sound energy on the inside of the sheet material. For example, LUMITEX® is a sound absorbing material manufactured by or for, distributed and/or sold by SoundSense LLC, Wainscott, N.Y. that also provides STC value when properly configured. Depending on materials of construction and configuration the structure will offer anything from the reduction of isolated frequencies to virtual sound isolation. The barrier layer is configured to block sound energy from passing through.

One version of the structure intended for noise reduction has only the sound absorbing material that is located on the inside of the sheet material adhered to or otherwise arranged to be integral with at least a part of a surface of the sheet material. The sound absorbing material, e.g., a sheet thereof, is adhered to the base sheet material by any means known to a person of ordinary skill in the art for adhering, attaching, sewing or applying one material to a surface or portion of a base sheet. The base sheet material may be cloth, a polymer, or any material chosen to accommodate the goals and aesthetics of the application.

Another version of the structure intended for noise reduction has the sound absorbing material that is located on the inside of the sheet material in addition to another layer that is a barrier layer, such as a loaded vinyl. Both materials are adhered to, or otherwise arranged to be, integral with each other. If necessary for aesthetic reasons, at least a part of the sheet material surface is a material befitting its application, such as a soft or patterned fabric, by any means known to a person of ordinary skill in the art for adhering, attaching, sewing or applying one material to a surface or portion of a surface of a sheet material comprising any synthetic or natural material, such as cloth or polymer.

The resulting sheet material with the sound absorbing layer, or sound absorbing layer with a barrier layer, is preferably flexible so that it may be configured to function as a boundary to unwanted sound, separating an environment in which there is an undesirable sound level (such as the sound of traffic, snoring or talking) from an environment where a lower ambient sound level is desired (or required), such as an internal environment substantially enclosed with the sheet material soundproofed with the sound absorbing layer.

Of course, the internal environment enclosed with the sheet material covered with the sound absorbing layer also operates to absorb sound generated in the internal environment so that noise level therein is lowered substantially.

In an embodiment, the invention includes a structure configured with an inner sound-limited or sound-reduced volume that is formed with a frame and a sheet material arranged about the frame to form and enclose sound-limited or sound-reduced volume. The sheet material has a base layer and a layer of sound-absorbing material provided on or integral with the base layer. The sound-limited or sound-reduced volume includes an entrance (means of egress) that in an open state allows for the sound entry to and exit from the sound-limited or sound-reduced volume and, in a closed or partially-closed state limits sound entry to and exit from the sound-limited or sound-reduced volume.

The frame of the structure can be constructed like a teepee, tent frame, or other shape that can be framed where the sheet material is part of the fabric configuration attached to the frame. The means of egress is preferably a flap. The flap is formed with a layer of sound absorbing material. In a variation, the sheet material includes two or more layers of sound absorbing material and may include a barrier. When a high level of acoustic separation is required, the flap or teepee entrance area is sufficiently long enough to act as a muffler. Accordingly, the two layers of sound absorbing material surround a base layer. The layer of sound-absorbing material is detachably connected to the base layer. The portion of the sheet material with the sound absorbing material, that transforms into the sound-limited or sound-reduced volume, not only minimizes sound entry but also minimizes an amount of sound exiting the inner volume, i.e., operates to soundproof the inner volume. The sheet material and sound-absorbing material used for the sound-limited or sound-reduced volume is preferably the same as the material from which the entrance is formed.

In another embodiment, the invention provides a structure configured with an inner, substantially sound-limited or sound-reduced volume. The structure comprises a frame and material, arranged about the frame to form and enclose the sound-limited or sound-reduced volume, wherein the material comprises a base layer and, attached to or integral therewith, at least one layer of sound absorbing material, at least one layer of sound barrier material, or at least one layer of both sound absorbing material and sound barrier material and, thereby, limits the sound entering or exiting the sound-limited or sound-reduced volume, through the material. Moreover, the sound-limited or sound-reduced volume includes an opening that in a fully open state allows for sound entry to and exit from the sound-limited or sound-reduced volume, through the opening, and in a closed or partially-closed state, limits sound entry to and exit from the sound-limited or sound-reduced volume, through the opening.

In another embodiment, a frame forms a hammock or basket structure upon which is provided a material having sound-absorbing properties. The hammock or basket preferably includes a flap, a canopy port or a hood portion, also formed to display sound-absorbing properties, which is manipulated to removably cover an opening in the hammock or basket. Most preferably, the flap, cover or canopy includes a layer of sound absorbing material, e.g., the material wrapped about the frame comprises at least one base layer, at least one sound absorbing layer and/or at least one sound barrier layer. Still more preferably, the material includes one or more layers of sound absorbing material.

The invention includes a structure configured with an inner, substantially sound-limited or sound-reduced volume. The structure comprises a frame; and material, arranged about the frame to form and enclose the sound-limited or sound-reduced volume. The material comprises a base layer and, attached to or integral therewith, at least one layer of sound absorbing material, at least one layer of sound barrier material, or at least one layer of both sound absorbing material and sound barrier material and, thereby, limits the sound entering or exiting the sound-limited or sound-reduced volume, through the material. The sound-limited or sound-reduced volume includes an opening that in a fully open state allows for sound entry to and exit from the sound-limited or sound-reduced volume, through the opening, and in a closed or partially-closed state, limits sound entry to and exit from the sound-limited or sound-reduced volume, through the opening.

The frame forms a hammock, basket, meditation pod, animal bed, snore reduction unit, wearable enclosure or other small structure. An interior of the sound-limited or sound reduced volume, when in a fully open state, operates as a sound absorber, and reduces a level of sound impinging on the head of a user present in the interior of the volume, or from the sound source in the interior from disturbing those outside of the structure. The structure preferably comprises a flap, a canopy or hood that is manipulated to cover the opening, wherein the flap, cover or canopy includes sound absorbing material. The material also may comprise at least one base layer, at least one sound absorbing layer and at least one sound barrier layer. Alternatively, the material may include two or more layers of sound absorbing material, or two or more layers of sound barrier material. The base layer is preferably a natural or synthetic fabric, and the material surrounding the frame is the same as the material forming the flap cover or canopy is the same.

In an embodiment, the invention provides a structure configured with an inner, substantially sound-limited or sound-reduced volume. The structure comprises a frame and material arranged about the frame to form and enclose the sound-limited or sound-reduced volume. The material comprises a base layer, where a first layer of sound-absorbing material is provided on or integral with at least one surface of the base layer. The sound-limited or sound-reduced volume includes an opening that in an open state allows for sound entry to and exit from the sound-limited or sound-reduced volume and in a closed state limits sound entry to and exit from the sound-limited or sound-reduced volume. A flap, canopy, or hood extends from the material arranged about the frame, which is moveable to cover or partially cover the opening and is moveable to uncover the opening.

In one form, the structure further comprises a second layer of sound-absorbing material provided on or integral with the base layer, on a surface of the base layer opposing a surface with the first layer of sound-absorbing material. Alternatively, the structure further comprises a layer of sound barrier material provided on or integral with the base layer or the first layer of sound-absorbing material.

BRIEF DESCRIPTION OF THE DRAWINGS

The invention will be described in conjunction with the following drawings in which reference numerals designate like elements and wherein.

DETAILED DESCRIPTION OF THE INVENTION

The following is a detailed description of the example embodiments of the invention as depicted in the accompanying drawings. The example embodiments are presented in detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1A:
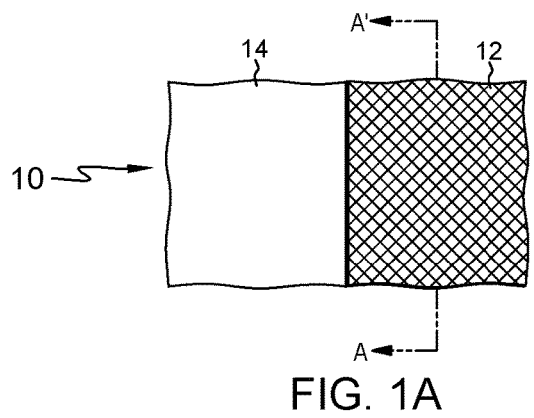
FIG. 1A Depicts a plan view of a surface of a sound attenuating sheet material formed by adhering sound absorbing or sound absorbing with a barrier material to approximately one half of one surface of the sheet of material.
Figure 1B:
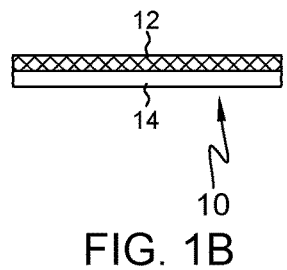
FIG. 1B Depicts a side cutaway view of the sheet material along the cut A-A' depicted in FIG. 1A.
Figure 5A:
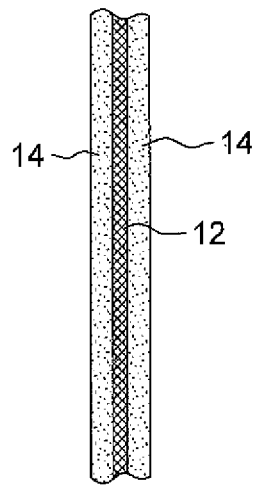
FIG. 5A Depicts a material sheet formed to include a layer of sound absorbing material sandwiched between an inner material layer and an outer material layer.
Figure 5B:
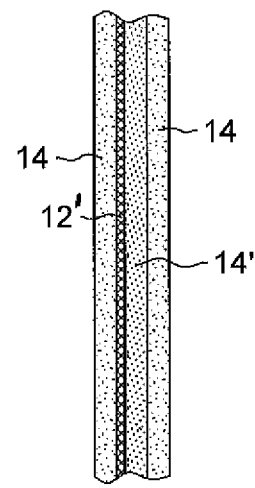
FIG. 5B Depicts a material sheet formed to include a layer of sound barrier material sandwiched between an inner material layer and at least two outer material layers.
Figure 5C:
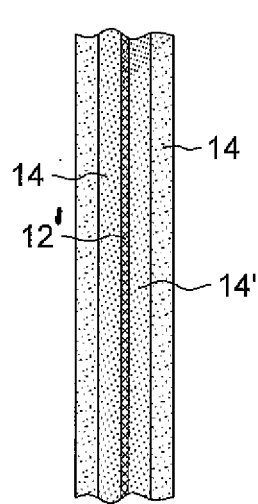
FIG. 5C Depicts a material sheet formed to include a layer of sound barrier material sandwiched between at least two inner material layers and at least two outer material layers.
Figure 5D:
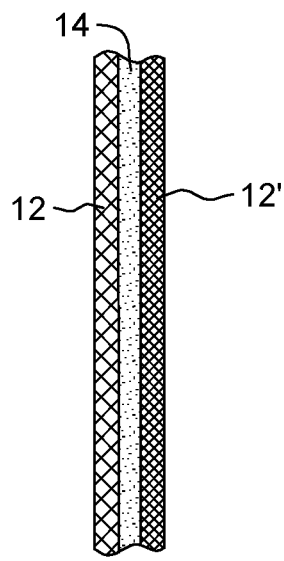
FIG. 5D Depicts a material sheet formed as a base layer to which are attached a layer of sound absorbing material and a layer of sound barrier material.
Figure 5E:
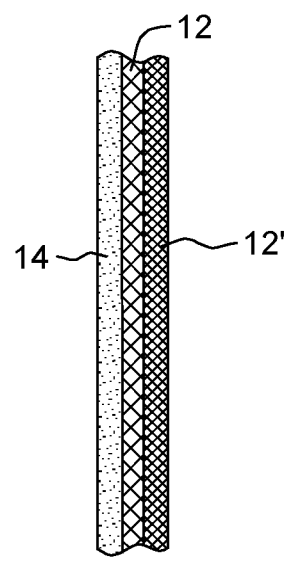
FIG. 5E Depicts a material sheet formed as a sound absorbing layer to which are attached a base layer and a layer of sound barrier material.
Figure 5F:
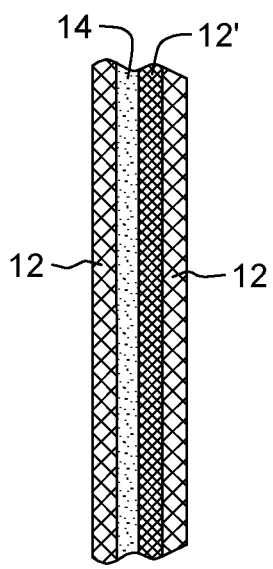
FIG. 5F Depicts a material sheet formed as a base layer to which is attached a sound absorbing layer and a layer of sound barrier material, and where a second layer of sound absorbing material is attached to the layer of sound barrier material.
Figure 5G:
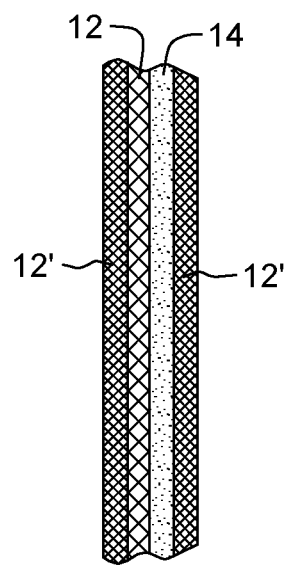
FIG. 5G Depicts a material sheet formed as a sound absorbing layer to which are attached a sound barrier layer and a base layer, and where a second layer of sound barrier material is attached to the base layer.

FIG. 1A depicts a plan view of the surface of a sound attenuating sheet material 10 formed by adhering a sound absorbing layer 12, or a sound barrier layer (or material) identified as 12' in FIGS. 5B, 5C), to approximately one half of one surface of the sheet of material 14. FIG. 1B shows a side cutaway view of sheet 10 along the cut A-A' depicted in FIG. 1A. Preferably, the sound absorbing 12 and/or barrier layer (or material) 12' is adhered to or integral with to cover the entire surface of the base layer 14 comprising material sheet 14.

Figure 2:
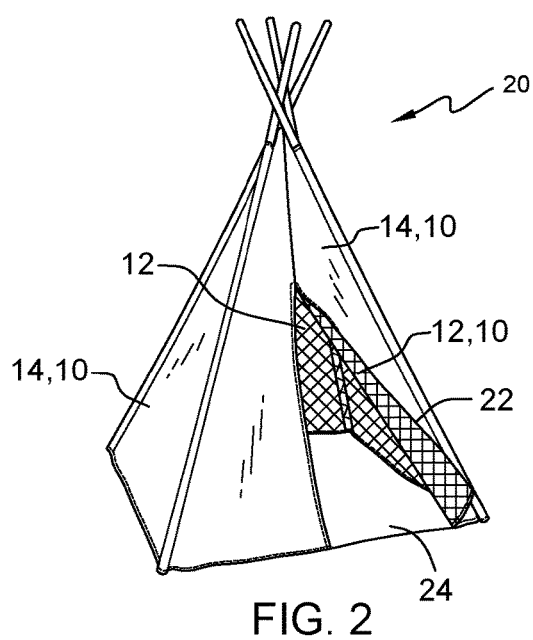
FIG. 2 Depicts a teepee structure that is formed with the sound attenuating sheet material including the sound absorbing layer or sound absorbing and barrier layer.
Figure 3:
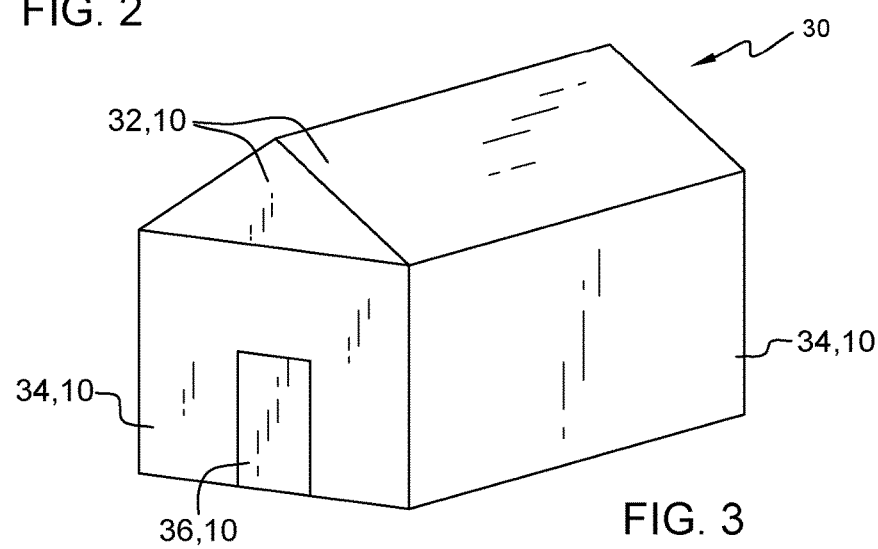
FIG. 3 Depicts a house or tent structure that is formed with the sound attenuating sheet material including the sound absorbing layer or sound absorbing and barrier layer.

FIGS. 2, 3 and 4 depict examples of structures that can be formed with the sound attenuating sheet material 10 formed with a base material layer 14 and a sound absorbing layer 12 and/or a sound barrier layer 12', adhered or integral therewith.

Whereas the STC and NRC of the sheet material is important to the design of any of the structures, it can vary according to the application. That is, in some applications it is more important that the inside of the structure have a comfortable sound decay time and only slightly reduce the outside noise entering the structure. There are other applications where a slight noise reduction from one side of the structure to the other is acceptable, but it is most important that the structure be light and easily portable. This is when the NRC criterion is more important than that of the STC. Other instances it is critical that the noise entering or exiting through the sheet material structure is significantly reduced if not eliminated to the opposite side of the structure. This is when the STC criterion becomes critical. Other instances the entrance needs to be open for easy access or airflow without an acoustically treated air flow chamber and the design of the flap or muffler type entrance tunnel then needs to match the criterion of the NRC and STC just stated.

FIG. 2 depicts a teepee 20 constructed with sound attenuating sheet material 10. The teepee is shown with a flap 22 in an open state, which flap would otherwise cover opening 24 in a closed state. When closed, some portion of the sound generated inside the teepee will not be transmitted to outside the teepee because of the sound attenuating sheet material 10. Likewise, the sound attenuating sheet material 10 limits sounds generated outside the teepee from passing through to enter the internal volume of the teepee. Perhaps as importantly, the sound generated inside the teepee is attenuated and softened inside the teepee to outside the teepee by the sound attenuating sheet material 10 (formed with the sound absorbing material or sound absorbing and barrier material 12 on some portion if not all of one surface).

The FIG. 2 construction is a basic tent design, e.g., an igloo-like tent, with fiberglass, wood, or metal supporting structure such that the tent/teepee is easily stored or transported in a very compact form. For that matter, a smaller tent or teepee-style structure constructed according to the inventive principles would be ideal for children to play in and not disturb those outside of the tent. The support poles for such a smaller structure, which would likely not require the portability of a tent, could be made of material other than that used for conventional tent poles, such as bamboo poles. The only requirement is that the poles for the smaller tent or teepee be sufficiently sturdy to withstand play, but light enough it can be disassembled and reassembled easily. All forms of the tent/teepees, or other small shaped structures would be constructed to allow for the airflow necessary which is required to "soundproof" a space. An acoustic viewing window could also be part of the structure.

A larger tent-like structure of any shape formed with the sound-attenuating sheet material 10 including a layer of sound absorbing material could accommodate an adult or a number of adults. Similar design and concept can be manufactured with the intended use being for adults to study, practice music, meditate, nap or talk on the phone without major disruption to those around them (and vice versa). The sound-attenuating sheet material 10 enables formation of structures enveloping an internal environment that "tunes" the noise down to make it a tolerable sound level, but does not eliminate noise entirely. Consequently, children could play freely inside the structure and an adult could work or have a phone conversation in the same room without having to compete with the volume, or sound level, of the children, but still have the ability to supervise the activity.

FIG. 3 depicts a house-like structure 30, configured around a shape-giving frame (not shown) covered with sound attenuating sheet material 10 (such as that depicted in FIGS. 1A and 1B). As shown, the sound attenuating sheet material 10 (with the sound-absorbing material on the inside surface) is covering the roof 32, the sides 34 and even the door 36, soundproofing the inside environment from the outside environment and vice versa, when the door is closed. Such a structure is intended only as an example embodiment, and does not need to have the walls 34 and roof as shown. For that matter, even a door may not be necessary, where a flap of the sound attenuating sheet material 10 or unraveling of the sound attenuating sheet material 10 could function to allow entry and exit from the structure 30 and act as an acoustical muffler. In such a case, the structure could be a tent, "lean to," cabana, hut, etc., and preferably portable with application for both indoor and outdoor usage, without limitation.

The structure built with the sound attenuating sheet material 10 formed with the sound absorbing material 12 on one surface also may be used advantageously to create modular sound environments. That is, the sheet/sound absorbing material 10/12, may form an outer surface of a multi-ply sheet, an inner surface of a multi-ply sheet or just a material sheet that separates an environment external to the modular sound environment and internal to the modular sound environment. Such modular sound environments allow for multiple activities of different volumes to "co-habitate" in the same space, by the inherent property of attenuating sound present therein without requiring a permanent wall that retracts or folds into or up against a wall or ceiling, etc.

Additionally, the sound attenuating sheet material 10 formed with the sound absorbing material 12 on one surface could be used to construct a small or medium enclosure (i.e., form an acoustic enclosure) designed to go over a dog cage. An opening, resembling something like an igloo opening, could be included in the covering to not only allow for air to flow to the dog, but also to serve as a muffler for the dog barking that is exiting the enclosure. By time the sound exits the opening it is reduced in dB level so that it is no longer disturbing to anyone in the vicinity. This second muffler entrance area height would depend on the size of the dog, as well as the noise reduction requirements. Often the opening, or even the full enclosure, can be just a simple arch shape.

An application to apply sound absorbing material 12 to the sheet 14 for sound attenuating can be a little different than that required for soundproofing. Design can include a full seam to a floor panel, etc., to create a more effective acoustic treatment, such as would be necessary when used for covering equipment, such as generators or computer fans.

Figure 4A:
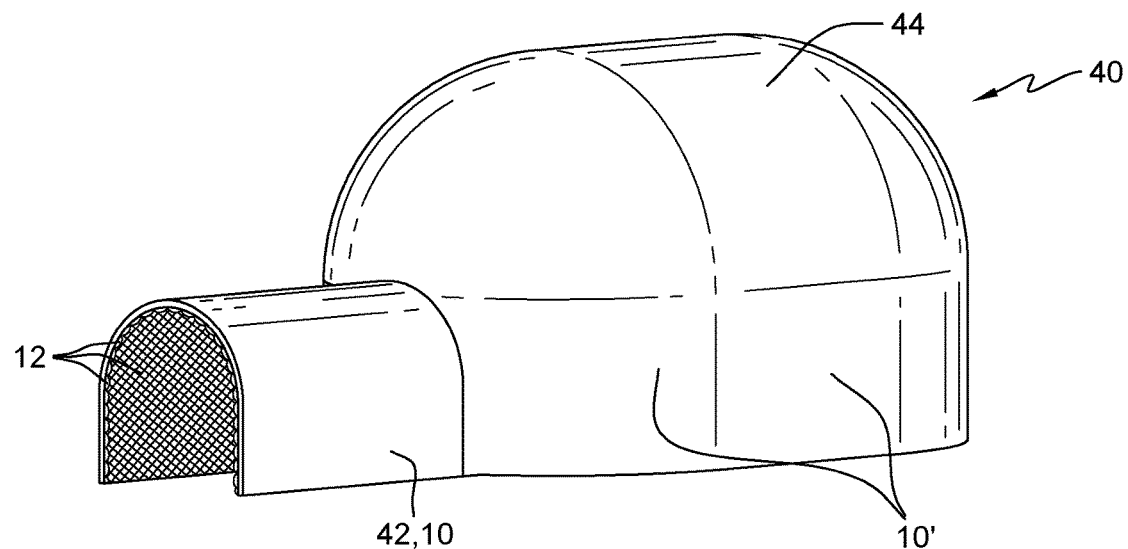
FIG. 4 Depicts an igloo-like structure formed with the sound attenuating sheet material including the sound absorbing layer or sound absorbing and barrier layer.
Figure 4B:
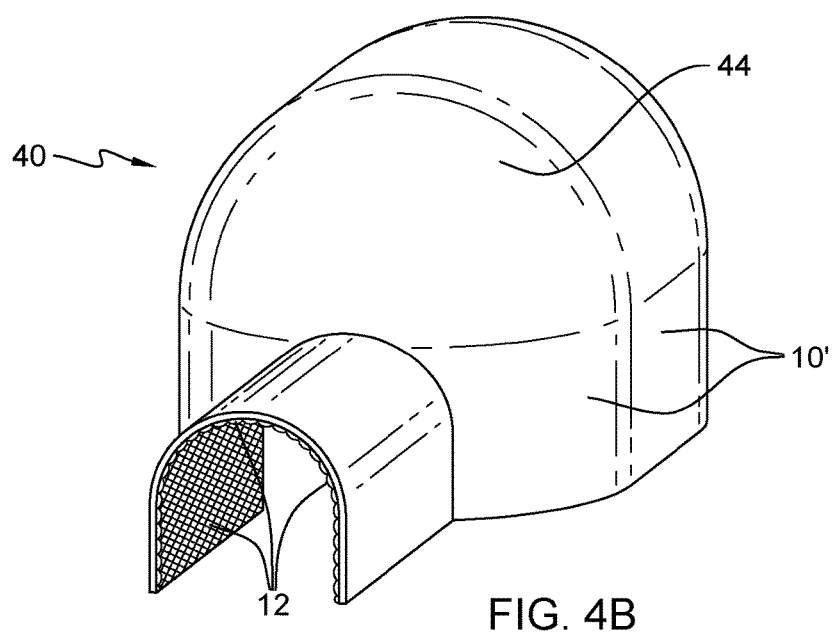

FIGS. 4A and 4B depict side and side (front) perspective views of an igloo-type structure or tent including attenuating sheet material 10 formed with a sound absorbing layer 12 adhered to or integral with a base material sheet 14. The igloo-type structure 40 is configured with a curved entrance 42, that can be of any desired shape, attached to a larger area 44 functioning as a work or sleeping area, that functions as a muffler, attenuating sound traveling through the length of the muffler (between the surface of the larger area 44 and the opening in the muffler 42, as shown) whether the sound is traveling in or out. The sheet material 10' covering the larger area 44 may comprise sheet material 10, or a variation on sheet material 10, or a sheet material that does not include the sound-absorbing material 12.

It is advantageous that the structures constructed include the attenuating sheet material 10 formed with a sound absorbing layer 12 adhered to or integral with a base material sheet 14 are portable, so that a sound controlled or sound reduced space in or out of the structure can be arranged in almost any environment and in particular, spaces surrounded by enclosures created as temporary structures, i.e., to be impermanent, like a tent, lean-to, igloo, cabana, changing area or napping/sleeping area.

FIG. 5A shows a material sheet formed with any number of layers of materials, including a layer of sound absorbing material 12. The layers may be said to be in sheets, for example, with an inner material layer 14 (formed for its look and feel and an outer material layer 14 surrounding the layer (or multiple layers) of sound absorbing material, operating a a quasi-barrier layer, as shown. The sound absorbing layer 12 (FIG. 5A) may be 1 to 6 or more layers of Lumitex material or other absorbers such as glass, foam or fiberglass. The outer material layer 14 defines the look and feel of the material sheets, for example, by its softness or ability to be written on. FIG. 5B depicts the embodiment of FIG. 5A, including an additional outer material layer 14, as shown, and wherein the sound absorbing layer 12 is replaced by a sound barrier layer 12'. FIG. 5C depicts the embodiment of FIG. 5A including at least 2 inner layers of material 14 and at least two outer layers of material 14, as well as a sound barrier layer 12', replacing sound absorbing layer 12 (FIG. 5A).

Another application would be to have an additional layer of material that inhibits radio frequency (RF) and similar frequency wave energy in combination with the attenuating sheet material. While the embodiment was described with only a single noise or sound absorbing layer, the sheet material also may include multiple noise or sound absorbing layers on a base layer without deviating from the scope and spirit of the invention. The second noise absorbing layer can function as a decoupler for potential low frequency noises. The sound waves emitted from any source proximate the user (or a portion thereof) are absorbed by the noise absorbing layer before it enters any reduced sound compartment, like a small space for speaking on a cell phone enclosed by the sheet portion comprising the structure (enclosure). With such a construction, a suitable sound transmission loss is achieved. The outer, inner or both noise absorbing layers preferably are made of a high NRC rated material, where "NRC" stands for noise reduction coefficient and represents the average amount of sound absorbed by the material. The NRC rating typically ranges from 0.01 to 1.0. NRC ratings above 1 (e.g., 1.03) are also possible. The higher the NRC rating, the greater the sound absorption of the material will be. The noise or sound absorbing layer(s) is/are chosen based upon the characteristics of the particular mechanism or noise to be absorbed.

Various materials are contemplated. In particular, the material forming the noise or sound absorbing/separating layer(s) is/are chosen for sound absorbing and/or sound barrier qualities and possibly the ability to operate as a heat insulator to enhance the ability to use the structure as a proper shelter. As such, the noise attenuation layer can differ from that forming the base layer. The layer may also be formed from a closely woven textile-like material made of any suitable material provided the material has suitable acoustic properties and withstands a predetermined temperature. A suitable adhesive can be used to secure the sound or noise absorbing and/or sound barrier layer to a base material layer. When multiple noise absorbing and/or barrier layers are provided, the layers can be formed from either the same material or a different material. Alternatively, the noise absorbing and/or barrier layer can be connected to a base or barrier layer when the garment is formed.

In an embodiment, for example, the invention provides a structure configured with an inner, substantially sound-limited or sound-reduced volume. The structure comprises a frame and material arranged about the frame to form and enclose the sound-limited or sound-reduced volume. The material may be formed as a sheet (weave, knit, sprayed, extruded, etc.). At least a portion of the sheet material includes sound-absorbing material; the sound-limited or sound-reduced volume includes an entrance that in an open state allows for sound entry to and exit from the sound-limited or sound-reduced volume and in a closed state limits sound entry to and exit from the sound-limited or sound-reduced volume. In one form, the material sheet embodies a base layer and wherein the sound-absorbing material is provided on or integral with at least one portion of the base layer. Alternatively, the material sheet embodies a base layer, the sound-absorbing material embodies a sheet and wherein the sheet of sound-absorbing sheet is provided on the at least one portion of the base layer.

The frame can be an igloo, teepee, tent, or habitable structure frame and the sheet material can be an igloo skin, a tent fabric, a teepee fabric, habitable or wearable structure material. The entrance comprises an opening that is covered with a flap. The flap includes sound absorbing material. In a variation, the sheet material includes two or more layers of sound absorbing material in the at least one portion. For that matter, the two layers of sound absorbing material surround the base layer.

The base layer is a natural or synthetic fabric. The sound-absorbing material is detachably connected to the base layer. The sheet material defining the sound-limited or sound-reduced volume minimizes an amount of sound entering the sound-limited or sound-reduced volume from outside the structure and an amount of sound exiting the sound-limited or sound-reduced volume from inside the structure. The sheet material defining sound-limited or sound-reduced volume is the same as the material forming the entrance is the same.

Figure 6A:
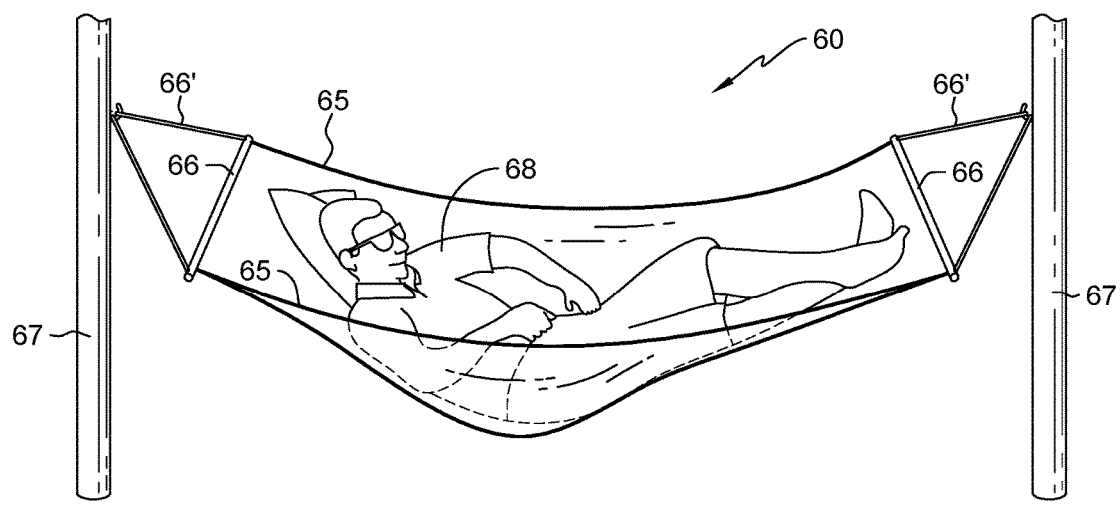
FIG. 6A Depicts an acoustic hammock configured according to the invention.

FIG. 6A depicts an acoustic hammock 60. The hammock 60 is formed with a sheet of material that is like the sheet 10, like the sheets depicted in FIGS. 5A-C, or like sheets comprising a base layer 14 and at least one layer of sound absorbing material 12 and/or at least one sound barrier layer 12', or multiple base layers 14 and at least one layer of sound absorbing material 12 and/or at least one sound barrier layer 12'. The sheet of material forming the acoustic hammock 60 is preferably one continuous sheet. The base layer 14, is typically the outer layer, and may be selected based on the aesthetics or intended use of the consumer or manufacturer.

The acoustic hammock 60 may be manufactured to look like a traditional hammock. The hammock 60, like a traditional hammock, has two opposing sides or edges 65 of the material sheet, where the opposing ends can include optional structural means 66, for separating the opposing side edges, as conventionally known. The hammock further includes means 66', such as a rope or chain, etc., for attaching the hammock 60, i.e., the respective structural means 66, or just the two ends of 65 to a tree, pole or other hammock support structure 67 that could even be formed to connect the two ends (not shown), at the opposing ends. Hence, the hammock 60 is typically in the shape of a sling structure, which creates a curved bottom. The hammock 60, however, is not limited thereto, and could instead be formed with multiple sections of material sheet, which are sewn together to realize a flat bottom during use. Whereas, as the distance of ear to 65 increases, so does the quietude, this picture shows that distance at a more minimal distance.

In many respects, the acoustic hammock 60 is like the aforementioned structures, such as the acoustic tent or igloo. However, when using the acoustic hammock 60, the user 68 may be said to be "on top" of (but substantially enveloped by) the structure 60, as distinguished from being beneath, or fully enclosed by the structures 20, 30, 40. So, while the user 68 is in the hammock 60, the sheet of material limits sound that might come into the inner hammock space (and would disturb the user) from under the hammock and, laterally from any of the 2 or 4 sides of the hammock (i.e., optional opposing ends (at structural means 66) and opposing sides 65). In the FIG. 6A embodiment, the space above the user 68 is substantially open for air. In this case, while much environmental sound is limited, some sound might enter the upper open volume, from above the user 68.

The sides of the Acoustic Hammock should be higher than a head height of a user 68 lying inside the hammock 60, to create a semi-isolated acoustic environment that will reduce the level of sound either entering or exiting the Acoustic Hammock. These sides limit incoming or outgoing sounds for the user (e.g., a person, baby or animal) semi-enclosed within the hammock semi-enclosure. In the fully open state, the interior or semi-enclosure exhibits highly efficient sound absorptive properties (or behavior), and thereby prevents amplification caused by reverberation, or reverberation amplification; this provides a state of organic quietude.

Figure 6B:
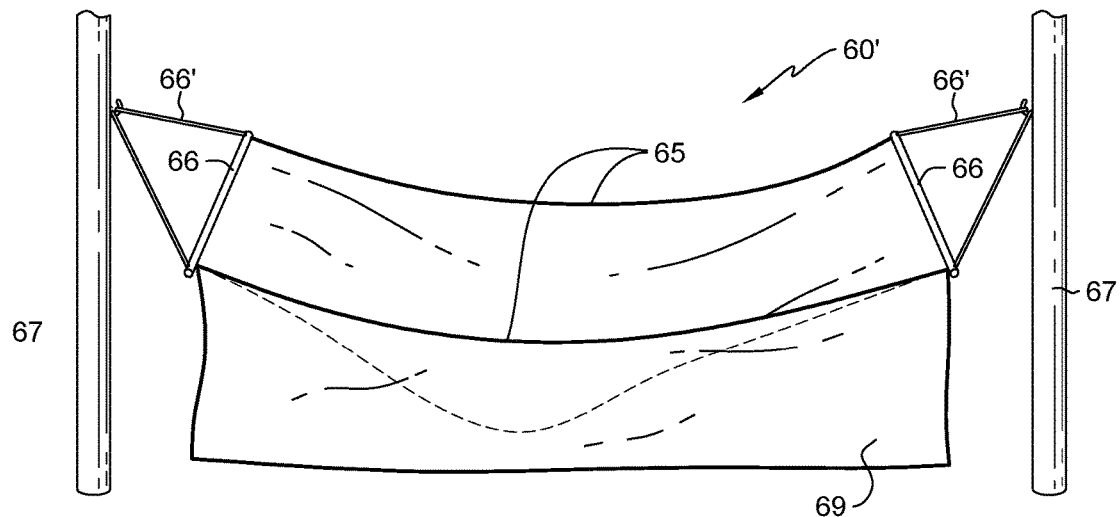
FIG. 6B Depicts the acoustic hammock of FIG. 6A, further configured with acoustic flaps.

In the hammock embodiment 60' depicted in FIG. 6B, an additional structure formed as flap 69, is included, which allows the user 68 to increase the ear to edge of hammock distance or cover him/herself, essentially blocking or limiting entry of sound from what would be an upper opening in the FIG. 6A hammock 60. The flap is attached to, or integral with and extending from, at least one side edge 65 of the hammock 60'. The flap 69 is preferably formed with the same material sheet composition of that forming the hammock structure itself, but is not limited thereto. The flap, however, in the preferred embodiment must be formed so that it exhibits some sound attenuating effect. As such, the flap 69, acts as a muffler. The muffler component (in the form of the flap 69), may be retracted and extended up or out, acting like a hood or a canopy. The acoustic hammocks 60, 60' may be used both indoors and outdoors.

Figure 6C:
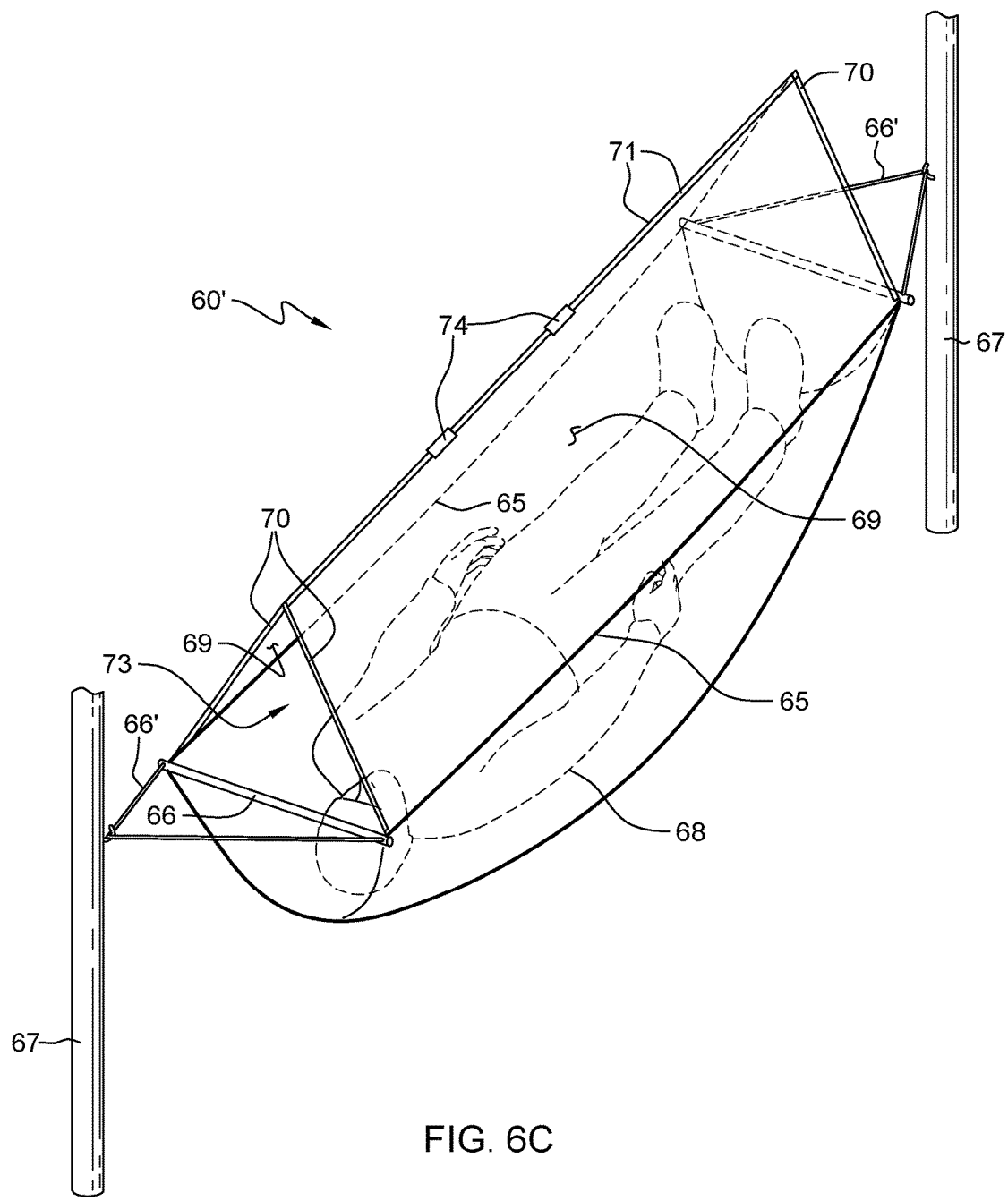
FIG. 6C depicts a perspective view of the acoustic hammock of FIG. 6B, where the flaps on both sides are raised and connected to form a semi-open enclosure.

FIG. 6C presents a perspective view of the hammock 60', where the flaps 69 on both sides are raised and connected to form a semi-open enclosure, with an opening 73 on both ends. The end edges 70 of each of the two flaps 69 are semi-rigid, as are the side edges 71. A fastening means, such as complementary Velcro fasteners 74, a zipper (not shown), complementary snap (not shown), etc., are positioned on or proximate the side edges 71, along the longitudinal length of the opposing flaps 69, to hold the flaps together above (and to form) the semi-enclosure (and to unfasten the flaps to open the hammock 60', as shown in FIG. 6B. The fastening means 74 allow for fastening and unfastening by the user 68 from inside the semi-open enclosure. Sound may enter the semi-enclosure (FIG. 6C), but is absorbed and attenuated by the inner surfaces of the sheet material forming the hammock 60' and the flaps 69.

In the FIG. 6C hammock, the opening between the edges 65 of the sheet material, or any seams formed in the hammock material sheet, may be trimmed with a rigid or semi rigid material to better allow for air flow to the user (or users) inside the hammock semi-enclosure. The rigidity at the edges 65 supports that the upper edges can be "flexed" open, maintaining the open state, and collapses to a less open state. This configuration is also beneficial to reduce the sounds of snoring. Hammock may have a flat bottom with semi-rigid sides. The hammock structure can be collapsible or foldable, so may be stored in a closet or in the trunk of a vehicle to easily accommodate all scenarios of use.

In a variation, the side edges 65 of hammock 60 (FIG. 6A) may include flexural support members (not shown), which enable the side edges to flex to a rigid state (and unflexed to a slack state). Once flexed, the rigid sides 65' maintain the hammock 60" in a relatively open hammock state. Upon flexing, back to an unflexed state, the hammock can then be maintained in a relatively closed or quasi-closed hammock state.

In another variation, the supports 67 would not be required and the hammock would be a partial enclosure that is wearable. That is, the hammock would wrap around the body and the body would serve as the support.

The acoustic hammock does not need to be hanging. If the sides are rigid or semi-rigid with a flat bottom the Acoustic Hammock would look like a canoe, boat, basket, animal bed or playpen. This can be useful whether it is placed in a home, backyard, outdoor camping space, or other situation where a person or animal is seeking or needful of quietude.

Figure 7A:
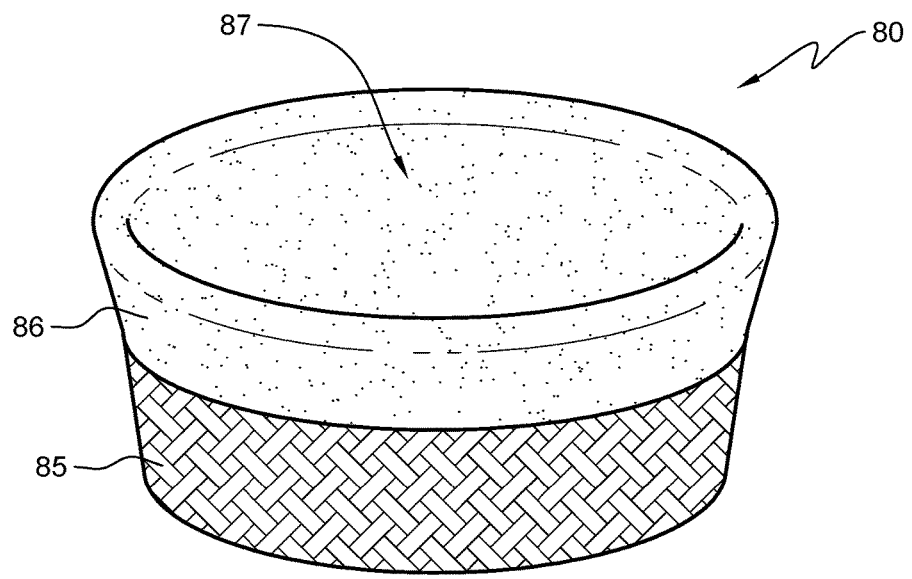
FIG. 7A Depicts an acoustic basket configured according to the invention.

FIG. 7A depicts an acoustic basket 80, constructed in accordance with the invention. The acoustic basket 80 is formed with a basket structure 85 upon which is mounted, positioned or attached, a liner 86 made of sound limiting material. That is, acoustic liner 86 is formed with a sheet of material that is like the sheet 10, the sheets depicted in FIGS. 5A-C, or like sheets comprising a base layer 14 and at least one layer of sound absorbing material 12' and/or at least one sound barrier layer 12, or multiple base layers 14 and at least one layer of sound absorbing material 12' and/or at least one sound barrier layer 12. If desired an acoustic viewing window can be part of the structure (not shown). The sheet of material forming the acoustic basket 80 is preferably one continuous sheet. The base layer 14, is typically the outer layer, and may be selected based on the aesthetics or intended use of the consumer or manufacturer. As shown in FIG. 7A, the liner 86 is seated and/or attached to cover the inside of the basket structure 85, where there is some overlap on the outer side or surface of the basket structure (as shown). As such an inner space of volume 87 is formed.

In a preferred embodiment the acoustic basket 80 can be placed on a floor so a child or animal could safely climb into it unassisted. The acoustic basket also can be used by children who are noise sensitive or are easily and highly disturbed by group noise. Another application could be naptime in or out of school. Alternatively, the basket could inhibit easy access of a baby, puppy, kitten, etc. The acoustic basket 80 may be placed inside or be part of a crib, playpen or bassinet to create an acoustically controlled environment while traveling or at home. As implied, the acoustic basket works equally well for animals.

Figure 7B:
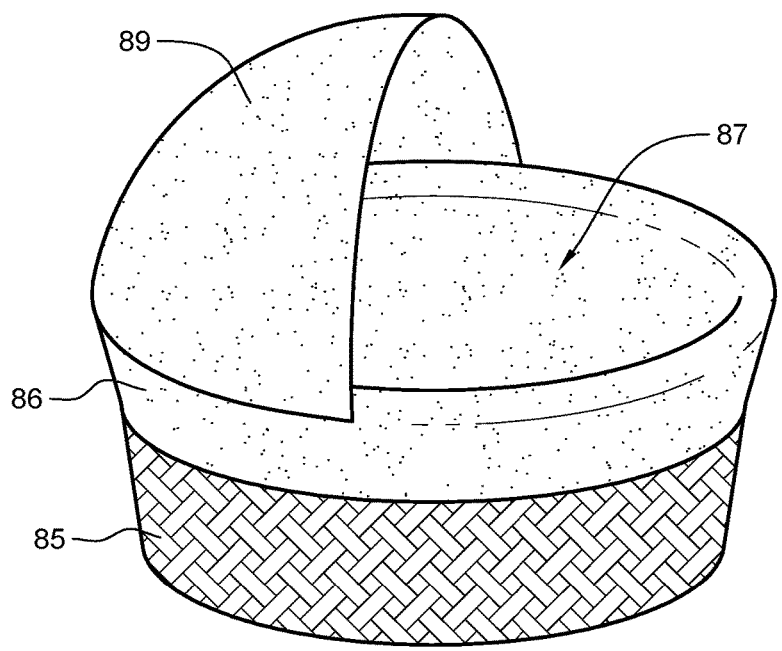
FIG. 7B Depicts the acoustic basket of FIG. 7A, further configured with at least a partial acoustic cover.

The sound-limiting sheet material 10 (FIGS. 1A, 1B, 5A, 5B, 5C) on the sides of the basket operate to muffle sound, with respect to the inner volume or space 87. The side(s) is typically must higher than the head of the user or animal contained therein. The material covering the sides of the basket minimizes or otherwise limits the sounds, for example, of a dog barking or howling proximate the basket (presumably with a child therein), which might otherwise pass into the basket's inner volume 87. The level of noise reduction can be further enhanced with one or more flaps or a hood 89, which operate to cover or partially cover the inner space of volume 87 (FIG. 7B). While the invention also includes an embodiment with a full cover configured to facilitate ventilation in the fully closed state, this embodiment is not shown in FIG. 7A or 7B. With the inventive acoustic basket, dogs or puppies in a basket are less likely to be disturbed by impulsive or transient sounds that result in unnecessary barking that would disturb a sleeping baby, person, or neighbor. As such, the bottom, sides and flaps or hood, embodying the sound absorbing and/or sound attenuating material (10) operate together as a sound muffler.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A structure configured with an inner, substantially sound-limited or sound-reduced volume, the structure comprising:
   a frame; and
   a material, arranged about the frame to form and partially enclose the sound-limited or sound-reduced volume, wherein the material comprises a base layer and, attached to or integral therewith, a layer of sound absorbing material and a layer of sound barrier material, to block sound energy from passing through the barrier layer, thereby limiting the sound entering or exiting the partially enclosed sound-limited or sound-reduced volume, through the material; and
   wherein the sound-limited or sound-reduced volume includes an opening that in a fully open state allows for sound entry to and exit from the opening, and in a partially-closed state, limits sound entry to and exit from the opening.

2. The structure of claim 1, wherein the frame forms a hammock, basket, meditation pod, animal bed, snore reduction unit, wearable enclosure or other small structure.

3. The structure of claim 1, wherein an interior of the sound-limited or sound-reduced volume, when in a fully open state, operates as a sound absorber, and reduces a level of sound impinging on a head of a user present in the interior of the volume, or from the sound source in the interior from disturbing those outside of the structure.

4. The structure of claim 1, further comprising a flap, a canopy or hood that is manipulated to removably cover the opening.

5. The structure of claim 4, wherein the flap, cover or canopy includes sound absorbing material.

6. The structure of claim 4, wherein the material surrounding the frame is the same as the material forming the flap cover or canopy is the same.

7. The structure of claim 1, where the material includes two or more layers of sound absorbing material.

8. The structure of claim 1, where the material includes two or more layers of sound barrier material, to block sound energy from passing through.

9. The structure of claim 1, wherein the base layer is a natural or synthetic fabric.

10. A structure configured with an inner, substantially sound-limited or sound-reduced volume the structure comprising:
    a frame; and
    a material arranged about the frame to form and partially enclose the sound-limited or sound-reduced volume;
    wherein the material comprises a base layer with opposing first and second surfaces;
    wherein a first layer of sound-absorbing material is provided on or integral with the first surface of the base layer;
    wherein a layer of sound barrier material is provided either on the second surface of the base layer or on the layer of sound absorbing material, to block sound energy from passing through the barrier layer;
    wherein the sound-limited or sound-reduced volume includes an opening that in an open state allows for sound entry to and exit from the sound-limited or sound-reduced volume and in a partially closed state limits sound entry to and exit from the sound-limited or sound-reduced volume;
    wherein a flap, canopy, or hood extends from the material arranged about the frame; and wherein the flap, canopy of hood is moveable to partially cover the opening and is moveable to uncover the opening.

11. The structure of claim 10, further comprising a second layer of sound-absorbing material provided on or integral with the second opposing surface of the base layer.

12. The structure of claim 11, further comprising a second layer of sound barrier material that is provided on the second layer of sound-absorbing material to block sound energy from passing through.

* * * * *